United States Patent
Tsujii et al.

(10) Patent No.: US 8,817,949 B2
(45) Date of Patent: Aug. 26, 2014

(54) RADIOGRAPHIC APPARATUS AND CONTROL METHOD THEREFOR

(75) Inventors: Osamu Tsujii, Kawasaki (JP); Hitoshi Inoue, Yokohama (JP); Masaaki Kobayashi, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 124 days.

(21) Appl. No.: 13/537,685

(22) Filed: Jun. 29, 2012

(65) Prior Publication Data

US 2013/0028499 A1 Jan. 31, 2013

(30) Foreign Application Priority Data

Jul. 25, 2011 (JP) ................. 2011-162430

(51) Int. Cl.
- *G06K 9/00* (2006.01)
- *A61B 6/00* (2006.01)
- *A61B 6/04* (2006.01)

(52) U.S. Cl.
CPC ............. *A61B 6/5205* (2013.01); *A61B 6/4452* (2013.01); *A61B 6/4405* (2013.01); *A61B 6/585* (2013.01); *A61B 6/4233* (2013.01); *A61B 6/5258* (2013.01); *A61B 6/0407* (2013.01)
USPC ........................................................ 378/95

(58) Field of Classification Search
None
See application file for complete search history.

(56) References Cited

U.S. PATENT DOCUMENTS

| | | | |
|---|---|---|---|
| 7,042,979 B2 | 5/2006 | Ikeda | |
| 7,142,705 B2 | 11/2006 | Inoue et al. | |
| 7,196,725 B1 | 3/2007 | Saigusa et al. | |
| 7,221,735 B2 | 5/2007 | Inoue | |
| 7,315,606 B2 | 1/2008 | Tsujii | |
| 7,386,157 B2 | 6/2008 | Tago et al. | |
| 7,945,015 B2 | 5/2011 | Tsujii et al. | |
| 7,994,481 B2 | 8/2011 | Yagi et al. | |
| 8,041,092 B2 | 10/2011 | Inoue | |
| 2005/0078793 A1* | 4/2005 | Ikeda | 378/98.8 |
| 2006/0169907 A1* | 8/2006 | Shinden | 250/370.09 |
| 2007/0127625 A1* | 6/2007 | Hornig | 378/167 |
| 2007/0165934 A1* | 7/2007 | Maac et al. | 382/132 |
| 2009/0026380 A1* | 1/2009 | Kito et al. | 250/370.09 |
| 2010/0067660 A1* | 3/2010 | Maurer et al. | 378/95 |
| 2010/0148076 A1* | 6/2010 | Nishino et al. | 250/363.02 |
| 2011/0057802 A1* | 3/2011 | Topfer et al. | 340/584 |
| 2011/0216884 A1 | 9/2011 | Tsujii et al. | |
| 2012/0018641 A1* | 1/2012 | Watanabe et al. | 250/354.1 |
| 2012/0039441 A1 | 2/2012 | Suwa et al. | |
| 2012/0051522 A1* | 3/2012 | Nishino et al. | 378/108 |
| 2012/0106704 A1* | 5/2012 | Maurer et al. | 378/65 |
| 2012/0114099 A1* | 5/2012 | Yoshida | 378/62 |

FOREIGN PATENT DOCUMENTS

| | | |
|---|---|---|
| JP | 2003-190126 A | 7/2003 |
| JP | 2006-158728 A | 6/2006 |
| JP | 2009-172250 A | 8/2009 |
| JP | 2009-178196 A | 8/2009 |

* cited by examiner

*Primary Examiner* — Atiba O Fitzpatrick
*Assistant Examiner* — Thomas A James
(74) *Attorney, Agent, or Firm* — Fitzpatrick, Cella, Harper & Scinto (57) ABSTRACT

A control portion (140) detects pressure information fluctuations applied to a radiation sensor portion (120), acquires a radiation image and an offset image from the radiation sensor portion (120) based on the detected pressure information fluctuations, and makes offset correction of the acquired radiation image using the acquired offset image.

15 Claims, 5 Drawing Sheets

RADIOGRAPHIC APPARATUS AND CONTROL METHOD THEREFOR

BACKGROUND OF THE INVENTION

1. Field of the Invention

The present invention relates to a radiographic apparatus and a control method therefor, and more particularly, to a control method based on pressure information fluctuations applied to a radiation sensor portion as an image detection unit.

Note that, description herein is made taking X-rays as an example of the radiation, but the present invention is not limited to X-rays, and electromagnetic waves such as γ-rays and α-rays and β-rays are also included in the radiation.

2. Description of the Related Art

An X-ray sensor in which a semiconductor is formed on a glass substrate is used in taking a still image and a moving image. Both when a still image is taken and when a moving image is taken, offset correction is made between offset images before and after X-ray exposure. However, the offset correction is made on the understanding that the offset image is stable during the image taking period.

The inventors of the present invention have found that, when an X-ray sensor is inserted under the body of a patient, body motion of the patient causes subtle changes (fluctuations) in the offset image. The offset image fluctuations are assumed to be due to pressure fluctuations applied to the X-ray sensor, and also, due to slimming down of the glass substrate on which the semiconductor is formed.

Japanese Patent Application Laid-Open No. 2009-178196 discloses a technology of using an X-ray sensor in conjunction with a pressure sensor. Specifically, a contact state is detected from the pressure sensed by the pressure sensor when a photographed body part of a patient is set in an electronic cassette, whether or not the pressure sensor within the range of a specified part is in a contact state is determined, and the result of the determination is reported to a radiographer via a display and a speaker.

Japanese Patent Application Laid-Open No. 2009-172250 discloses a technology of, when the absolute value of the difference between the area of a set contact range between an X-ray sensor and a subject and the area of the actual contact range is larger than an allowable threshold value of the area, determining that the photographed body part of a patient is not set in the electronic cassette in a desired state, and reporting the determination to a radiographer.

On the other hand, Japanese Patent Application Laid-Open No. 2003-190126 discloses a technology relating to a method of collecting offset images of an X-ray sensor. Specifically, first, prior to taking a radiation image, the rate of change is calculated of an output signal of an integrator in a predetermined time period from a reset of the integrator to a supply of an exposure start signal. This rate of change is used to calculate an offset voltage signal at an arbitrary time, which is supplied to a voltage correction circuit. By correcting an output signal of the integrator after the exposure starts with the offset voltage signal and then supplying the corrected output signal to an X-ray control portion, exposure of the applied X-rays is controlled.

Further, in Japanese Patent Application Laid-Open No. 2006-158728, radiation is applied from a radiation emitting portion to a subject with a predetermined period. A subject image based on the applied radiation is detected by a photoelectric conversion circuit, and an offset image is periodically acquired. In response to a change in the acquired periodical offset image, the radiation application period of the radiation emitting portion and the period of reading a subject image from the photoelectric conversion circuit are controlled. Immediately after the start of photographing where offset fluctuations occur, offset photographing and subject photographing are alternately performed so as to correctly make offset correction of the subject image. When the offset becomes stable, subject photographing may be continuously performed at a high frame rate.

An X-ray sensor in which a semiconductor is formed on a glass substrate is used in, for example, portable roentgenographic apparatus, and the X-ray sensor is inserted under the body of a patient and an image is taken. As described above, the inventors of the present invention have found that, when the X-ray sensor is inserted under the body of a patient, body motion of the patient causes subtle changes (fluctuations) in the offset image. The offset image fluctuations cause an error in the offset correction, which degrades the quality of the diagnostic image. Fluctuations of an offset image are assumed to be due to pressure fluctuations applied to the X-ray sensor, but the actual cause has not been identified yet. Body motion of a patient is broken down into single body motion and periodical body motion. Periodical body motion includes heartbeat and respiratory body motion. The periods of the heartbeat and respiratory body motion are 0.5 seconds to 3 seconds.

SUMMARY OF THE INVENTION

The present invention has been made in view of such a problem, and an object of the present invention is to acquire a radiation image with only a small error in offset correction even under circumstances in which pressure information fluctuations applied to a radiation sensor portion as an image detection unit occur.

In order to realize the above-mentioned functions, according to the present invention, there is provided a radiographic apparatus for controlling a radiation source which applies radiation, including: a radiation sensor for acquiring spatial intensity distribution of radiation as two-dimensional image data; and a control unit for controlling acquisition of the image data by the radiation sensor based on fluctuation information on a pressure applied to the radiation sensor.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Preferred embodiment(s) of the present invention will be described in detail in accordance with the accompanying drawings.

Embodiments for carrying out the present invention are described in the following with reference to the attached drawings.

(First Embodiment)

Figure 1:
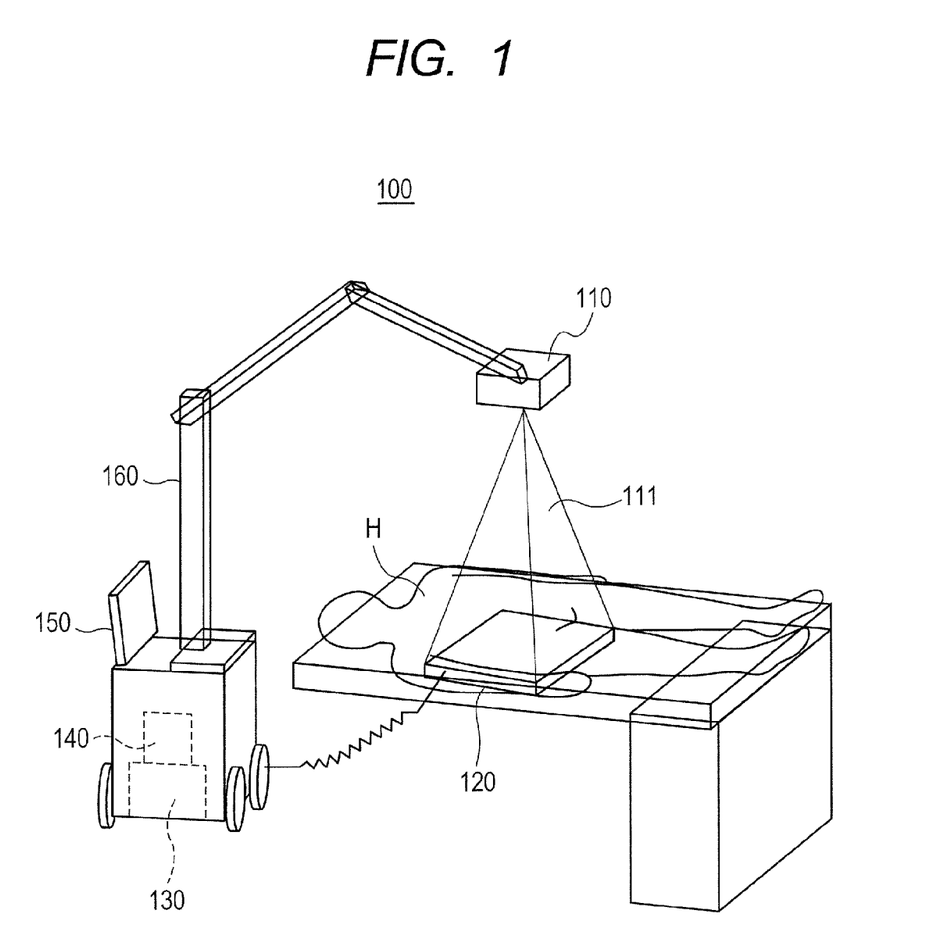
FIG. 1 is a schematic view illustrating a schematic exemplary configuration of a portable roentgenographic apparatus (portable radiographic apparatus) according to a first embodiment of the present invention.

FIG. 1 is a schematic view illustrating a schematic exemplary configuration of a portable roentgenographic apparatus (portable radiographic apparatus) according to a first embodiment of the present invention.

A portable roentgenographic apparatus 100 illustrated in FIG. 1 includes an X-ray source (radiation source) 110, an X-ray sensor portion (radiation sensor portion) 120, a power supply portion 130, a control portion 140, a display portion 150, and an arm 160.

The X-ray source 110 attached to an end of the arm 160 generates X-rays 111 and applies the X-rays 111 to a subject H which is a patient.

The X-ray sensor portion 120 receives X-rays which pass through the subject H under a state in which the X-rays 111 from the X-ray source 110 are applied to the subject H, converts the received X-rays into electric signals (image signals) based thereon, and detects the electric signals as an X-ray image (radiation image). Further, the X-ray sensor portion 120 detects an offset image under a state in which the X-rays 111 from the X-ray source 110 are not applied to the subject H. Here, the X-ray sensor portion 120 for detecting the X-ray image (radiation image) and the offset image forms an "image detection unit".

The power supply portion 130 supplies power (voltage, etc.) to the X-ray source 110, the X-ray sensor portion 120, the control portion 140, and the display portion 150.

The control portion 140 controls the entire operation of the portable roentgenographic apparatus 100.

Specifically, in this embodiment, the control portion 140 first detects pressure information fluctuations applied to the X-ray sensor portion 120. The control portion 140 for detecting pressure information fluctuations forms a "pressure information fluctuation detection unit".

Further, when a coefficient of pressure fluctuation based on the detected pressure information fluctuations is smaller than a threshold value, the control portion 140 acquires the X-ray image (radiation image) and the offset image from the X-ray sensor portion 120. The control portion 140 for acquiring the X-ray image (radiation image) and the offset image forms an "acquisition unit".

Further, the control portion 140 makes offset correction of the acquired X-ray image (radiation image) using the acquired offset image. The control portion 140 for making offset correction forms an "offset correction unit".

The display portion 150 displays an image based on electric signals (image signals) generated by the X-ray sensor portion 120, various kinds of information, and the like.

Figure 2A:
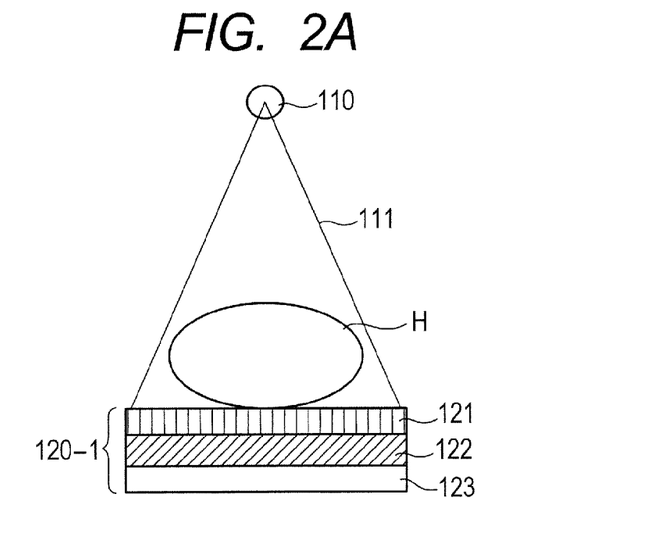
FIGS. 2A and 2B are schematic views illustrating detailed exemplary configurations of an X-ray sensor portion (radiation sensor portion) illustrated in FIG. 1.
Figure 2B:
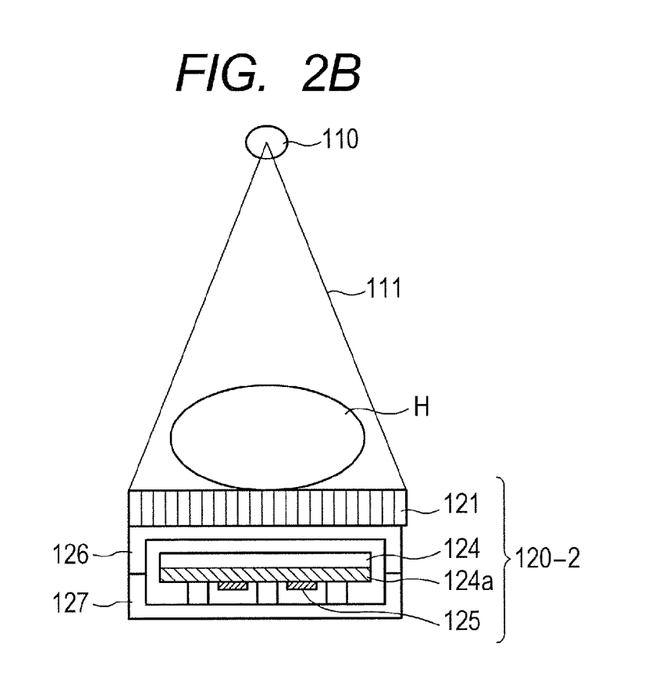

FIGS. 2A and 2B are schematic views illustrating detailed exemplary configurations of the X-ray sensor portion (radiation sensor portion) 120 illustrated in FIG. 1.

In this embodiment, as illustrated in FIGS. 2A and 2B, the X-ray sensor portion 120 includes an anti-scatter grid, a pressure sensor, and an X-ray sensor formed on a sensor substrate. The X-ray sensor includes a glass substrate as the sensor substrate, a semiconductor layer, and a fluorescent layer. The pressure sensor may be placed on a radiation receiving surface of the sensor substrate, on the back (rear surface) of the sensor substrate, or on the periphery of the sensor substrate. As the pressure sensor, a resistance film type, a surface acoustic wave type (ultrasonic type), a wire resistance strain gauge, or a microswitch may be used. The resistance film type and the surface acoustic wave type are placed so as to be sheet-like with respect to the sensor substrate. The wire resistance strain gauge and the microswitch are placed discretely with respect to the sensor substrate.

FIG. 2A illustrates an X-ray sensor portion 120-1 for receiving X-rays which pass through the subject H under a state in which the X-rays 111 from the X-ray source 110 are applied to the subject H which is a patient. The X-ray sensor portion 120-1 illustrated in FIG. 2A includes a grid 121, a pressure sensor 122, and an X-ray sensor 123. Here, the pressure sensor 122 is placed on a radiation receiving surface of a sensor substrate which forms the X-ray sensor 123. In this case, X-rays which pass through the subject H and enter the X-ray sensor 123 are attenuated by the pressure sensor 122 to lower the sensitivity of the X-ray sensor 123. When the pressure sensor 122 illustrated in FIG. 2A is placed on the radiation receiving surface of the sensor substrate, a transmission image of the pressure sensor 122 is projected onto the sensor substrate. The transmission image of the pressure sensor 122 is required to be canceled by gain image correction. Here, the gain image correction is made by dividing an X-ray image when the subject H does not exist by an X-ray image when the subject H exists.

FIG. 2B illustrates an X-ray sensor portion 120-2 for receiving X-rays which pass through the subject H under a state in which the X-rays 111 from the X-ray source 110 are applied to the subject H which is a patient. The X-ray sensor portion 120-2 illustrated in FIG. 2B includes the grid 121, an X-ray sensor 124 which includes a sensor substrate 124, and a pressure sensor 125. Further, the X-ray sensor 124 and the pressure sensor 125 are provided within a housing which includes an upper housing 126 and a lower housing 127. Here, the pressure sensor 125 is formed on the back of the sensor substrate which forms the X-ray sensor 124. Specifically, the pressure sensor 125 is placed on the back of a surface of the X-ray sensor 124 on which the X-rays are incident. In this case, there are no problems of the attenuation of X-rays which pass through the subject H and enter the X-ray sensor 124 and the projection of the transmission image of the pressure sensor 125 which are described with reference to FIG. 2A. Therefore, it is preferred to place the pressure sensor 125 on the back of the sensor substrate as illustrated in FIG. 2B.

Figure 3:
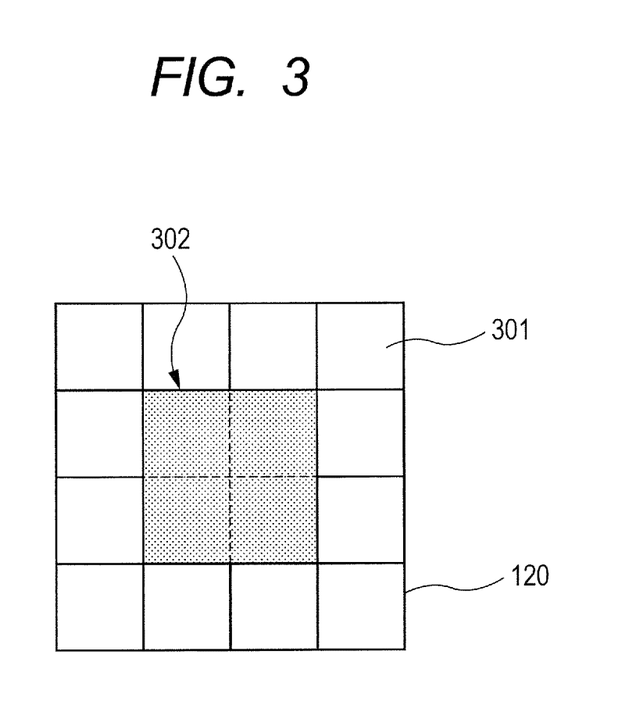
FIG. 3 is a schematic view illustrating an exemplary important subregion in an entire sensor substrate illustrated in FIG. 2B.

As illustrated in FIG. 2B, when the pressure sensor 125 is placed on the back of the sensor substrate 124a, there are a case in which the pressure sensor is placed on the entire surface of the sensor substrate and a case in which the pressure sensor is placed so as to correspond to only part of the sensor substrate. Here, when the pressure sensor is placed so as to correspond to only part of the sensor substrate, the pressure sensor is placed so as to correspond to a central area of the sensor substrate (FIG. 3). The reason is that, generally, an important portion of an image of the subject is assumed to be projected onto the central area of the sensor substrate. The pressure sensor is required to detect pressure applied to the sensor substrate with small attenuation. Therefore, coupling between the pressure sensor and the sensor substrate is required to be rigid.

FIG. 3 is a schematic view illustrating an exemplary important subregion in the entire sensor substrate illustrated in FIG. 2B. As illustrated in FIG. 2B, a surface of the radiation sensor to which radiation is applied is divided into a plurality of subregions 301, and, among the subregions 301, there is an important subregion 302 which exists in a central area of the surface.

Although not shown in FIGS. 2A and 2B, the pressure sensor may also be placed on the periphery of the sensor substrate (outside the radiation receiving portion). In this case, the pressure applied to the central area (important subregion) of the sensor substrate illustrated in FIG. 3 cannot be directly measured, but addition as noise to the image of X-rays scattered by the pressure sensor may be eliminated.

On the other hand, when a housing including the X-ray sensor which has the sensor substrate is integrally deformed when pressure is applied thereto from the outside, the pressure sensor may be fixed to a rear surface of the housing or on the periphery of the radiation receiving surface.

The pressure sensor outputs pressure values at a plurality of locations. The pressure values with regard to the respective locations from the pressure sensor are compiled by the control portion 140. There is a case in which the pressure values are compiled with regard to the respective 4×4 subregions as illustrated in FIG. 3. There is a case in which pressure values with regard to the 16 subregions illustrated in FIG. 3 are averaged with the same weight to calculate the pressure information. On the other hand, there is a case in which the pressure values with regard to the 16 subregions illustrated in FIG. 3 are averaged with different weights to calculate the pressure information. When the respective subregions are weighted, weight coefficients of the respective subregions are determined based on photographing information.

Here, the photographing information is transferred from a radiation information system RIS (not shown) via a network to, for example, the control portion 140. The photographing information includes photographed body part information such as a head, a chest, an abdomen, or a limb, and patient information such as the weight of the patient and the height of the patient. When the photographed body part is a chest or an abdomen, for example, the subregions are evenly weighted. When the photographed body part is a head or a limb, for example, the weight coefficient in the central area is set to be larger. Further, when the weight of the patient is heavy, for example, the entire weight coefficients are set to be smaller, because otherwise the calculation is late for the timing at which the photographing becomes possible. When the height of the patient is small, for example, the weight coefficient in the central area is set to be larger. Further, it is also possible that the weight coefficient in the central area of the sensor substrate is set to be always larger than the weight coefficient in the peripheral region. The reason is that, generally, a region of which an image is to be taken is adjusted to be in the central area of the X-ray sensor portion 120.

The pressure values of the pressure sensor are periodically sampled by the control portion 140.

Figure 4:
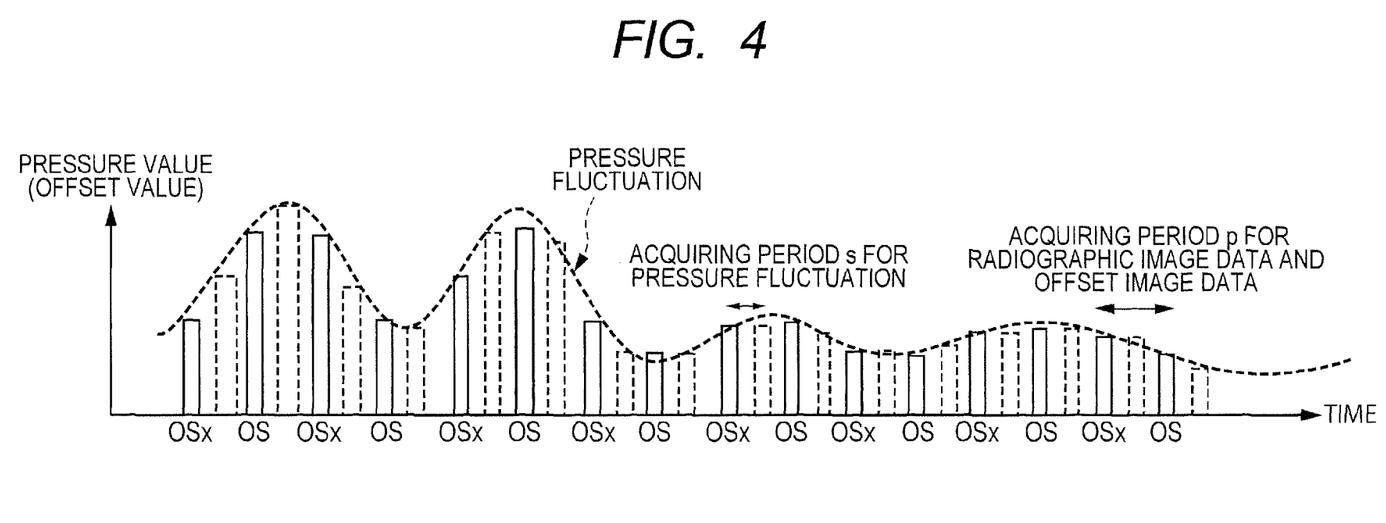
FIG. 4 is a characteristic diagram illustrating an exemplary pressure fluctuation curve of the first embodiment of the present invention.

FIG. 4 is a characteristic diagram illustrating an exemplary pressure fluctuation curve which is pressure fluctuation information according to the first embodiment of the present invention. In FIG. 4, the horizontal axis denotes time, while the vertical axis denotes pressure value. An acquiring period s for sampling pressure values may be empirically determined or may be determined by a condition of driving the X-ray sensor portion 120. Here, the condition of driving the X-ray sensor portion 120 is an acquiring period p for an X-ray image and an offset image.

There is a relationship of s≤p between the acquiring period s for sampling pressure values and the acquiring period p for an X-ray image and an offset image. This means that the error in offset correction cannot be predicted unless the pressure fluctuations are observed in the acquiring period s which is shorter than the acquiring period p for an X-ray image and an offset image. Therefore, the pressure fluctuation information is thought to be calculated based on the offset image. The acquiring period p for an X-ray image and an offset image is, when 15 moving images are taken per second, about 30 msec. Here, it is assumed that an X-ray image and an offset image are alternately collected. Further, the acquiring period p for an X-ray image and an offset image is, when still images are taken, about 1 sec. In the case of a portable roentgenographic apparatus, serial taking of 3 images per second is mainly carried out, and thus, even when still images are taken, the pressure values are sampled under a state in which the acquiring period s is constant and is about 150 msec.

Solid lines and broken lines in FIG. 4 denote the timing at which the sampled pressure values are collected. The solid lines in FIG. 4 denote the timing at which images are collected by the X-ray sensor portion 120. OSx in solid lines denotes the timing at which an X-ray image is collected, while OS in solid lines denotes the timing at which an offset image is collected. When the difference between the timing OSx at which an X-ray image is collected and the timing OS at which an offset image is collected thereafter (or therebefore) is large, it means that an error in the offset correction is large. In FIG. 4, on the right side of the time axis, the difference between the timing OSx at which an X-ray image is collected and the timing OS at which an offset image is collected is small, and thus, qualitatively, by taking an X-ray image on the right side of the time axis, an image having a small error in the offset correction may be acquired. Specifically, it is desired to have a configuration in which, when the amount of fluctuations acquired from the above-mentioned fluctuation information is equal to or smaller than a predetermined value, the control portion determines that an image with a small error in the offset correction may be acquired, and thus, allows acquisition of image data.

When X-rays are directed, the timing OSx at which an X-ray image is collected and which corresponds to the X-ray image at that time is estimated. Therefore, there are various alternatives of adopting the timing OS at which an offset image is collected immediately before the exposure, adopting the timing OS at which an offset image is collected immediately after the exposure, and adopting averaging of the timing OS at which an offset image is collected before the exposure and the timing OS at which an offset image is collected after the exposure. In order to shorten delay in displaying an X-ray image, it is good to adopt the timing OS at which an offset image is collected immediately before the exposure.

Figure 5:
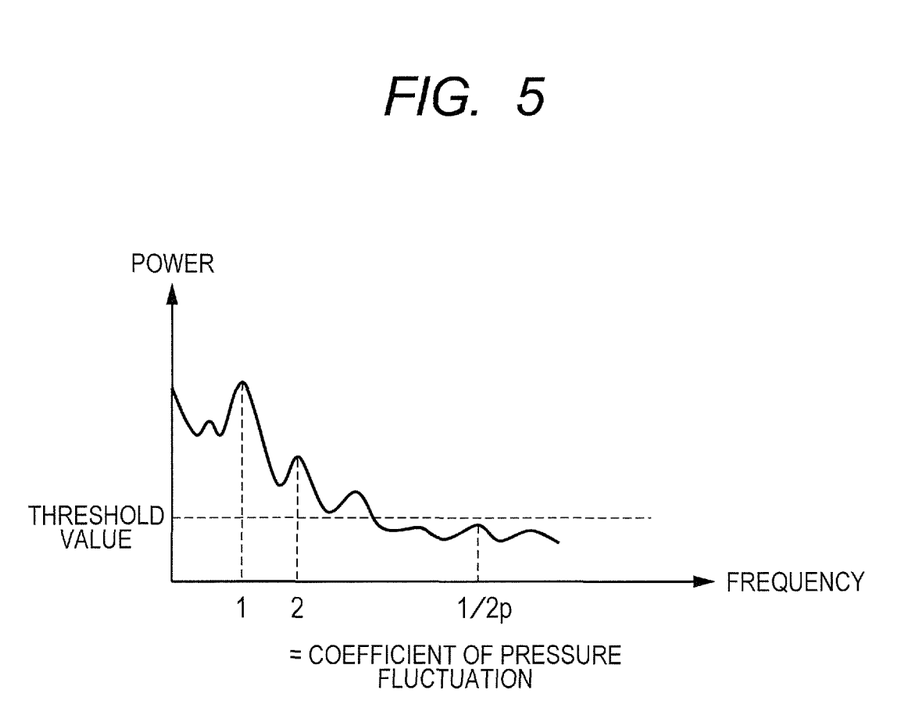
FIG. 5 is a characteristic diagram illustrating an exemplary relationship between frequency analysis of pressure fluctuations and coefficient of pressure fluctuation of the first embodiment of the present invention.

FIG. 5 is a characteristic diagram illustrating an exemplary relationship between frequency analysis of pressure fluctuations and coefficient of pressure fluctuation according to the first embodiment of the present invention. Pressure applied to the X-ray sensor portion 120 includes body motion due to respiration, and heartbeat of the subject which is a patient. By performing frequency analysis of the pressure fluctuations, pressure fluctuations at high frequencies and pressure fluctuations at low frequencies may be discriminated. Fluctuations at high frequencies are characterized by weak power. As a qualitative argument, pressure fluctuations at high frequencies having weak power do not cause an error in the offset correction.

Here, as the standard of high frequencies, the acquiring period p for an X-ray image and an offset image is used. In FIG. 5, as the standard of high frequencies, 1/2p is adopted (the standard may also be 1/p). Power of fluctuations having a frequency of 1/2p is herein referred to as a "coefficient of pressure fluctuation". Specifically, the coefficient of pressure fluctuation is calculated based on the acquiring period p for an X-ray image and an offset image. When the coefficient of pressure fluctuation is smaller than the predetermined threshold value, the error in the offset correction is expected to be smaller than a predetermined standard. The frequency analysis of the pressure fluctuations is performed sequentially and updated in real time by the control portion 140.

In this embodiment, the control portion 140 detects pressure information fluctuations applied to the X-ray sensor portion 120. When the coefficient of pressure fluctuation based on the detected pressure information fluctuations is smaller than the threshold value, an X-ray image (radiation image) and an offset image are acquired from the X-ray sensor portion 120. The control portion 140 uses the acquired offset image to make offset correction of the acquired X-ray image (radiation image). Specifically, taking of the X-ray image becomes possible when the coefficient of pressure fluctuation becomes smaller than the predetermined value (threshold value).

Note that, the coefficient of pressure fluctuation may be calculated as follows.

For example, the coefficient of pressure fluctuation may be calculated after the X-ray sensor portion 120 is broken down into a plurality of subregions as illustrated in FIG. 3. In this case, when the control portion 140 acquires an X-ray image (radiation image) and an offset image from the X-ray sensor portion 120, the coefficient of pressure fluctuation is set to be smaller than the threshold value in the central area (important subregion) of the X-ray sensor portion 120.

(Second Embodiment)

In the first embodiment, the pressure information is measured using the output of the pressure sensor associated with the X-ray sensor. However, the pressure information may be acquired not only by using the output of the pressure sensor but also by using, for example, an offset image taken by the X-ray sensor portion 120, or, output of an acceleration sensor placed in the X-ray sensor portion 120. Based on the pressure information acquired by any one of these, the coefficient of pressure fluctuation may be calculated. As a term which includes all of these, a "coefficient of pressure information fluctuation" is defined. In the following, an embodiment is described in which the coefficient of pressure information fluctuation is calculated using an offset image taken by the X-ray sensor portion 120.

Factors in offset image fluctuations empirically include temperature fluctuations and pressure fluctuations. The period of temperature fluctuations is very long compared with the acquiring period p for an X-ray image and an offset image, and thus, it is not considered necessary to take the temperature fluctuations into consideration with regard to the error in the offset correction. It follows that, by observing the offset image for a short period of time, the pressure fluctuations may be measured. A "short period of time" as used herein is a period of time from when an operator inserts the X-ray sensor portion 120 under the subject H which is a patient and to when the operator presses down an X-ray exposure start button (not shown) in order to take an X-ray image. Specifically, the short period of time begins when an order to take an image of the patient reaches the control portion 140, when the operator inputs the name of the patient, or when a photographed body part button is selected to confirm a photographing request. Here, the short period of time is specified because a large amount of electric power is consumed in an amplifier circuit (AMP) (not shown) of the X-ray sensor portion 120 in order to capture an offset image which results in a temperature rise of the X-ray sensor portion 120.

The solid lines and the broken lines in FIG. 4 denote the timing at which an offset image is collected. Specifically, the timing at which an offset image is collected has a period of p/2, that is, twice as often as the acquiring period p for an X-ray image and an offset image calculated by a frame rate with which the operator attempts to photograph. Further, for the purpose of suppressing a temperature rise of the X-ray sensor portion 120, the timing at which an offset image is collected may have a period of p.

There is a plurality of methods of calculating offset image fluctuations. The simplest method is to sum squares of differences in the respective pixels in a scaled down image. A method in which squares of differences in the respective pixels are summed with attention being focused on the central area (important subregion) of the X-ray sensor portion 120 illustrated in FIG. 3 may also be used. Further, as described in the first embodiment, the part of the X-ray sensor portion 120 on which attention should be focused may be determined using the patient information and the photographed body part information. Still further, the method of calculating offset image fluctuations may use a sum of absolute values of differences in the respective pixels instead of the sum of squares thereof. Frequency analysis of the sum of squares, the sum of absolute values, or an average of differences in the respective pixels is performed to calculate the coefficient of pressure fluctuation. When the coefficient of pressure fluctuation becomes smaller than the predetermined threshold value, the control portion 140 acquires an X-ray image (radiation image) and an offset image from the X-ray sensor portion 120. The control portion 140 uses the acquired offset image to make offset correction of the acquired X-ray image (radiation image). Specifically, the control portion 140 enables taking an X-ray image when the coefficient of pressure fluctuation becomes smaller than the predetermined value (threshold value). When taking an X-ray image becomes possible, the display portion 150 displays that taking the X-ray image is possible, and operation by an operator of pressing down the X-ray exposure start button is enabled.

(Third Embodiment)

In the above-mentioned embodiments, taking an X-ray image becomes possible when the coefficient of pressure information fluctuation (coefficient of pressure fluctuation) becomes smaller than the predetermined value (threshold value). It is necessary to adjust the threshold value depending on the conditions of generating X-rays (conditions of generating radiation) by the X-ray source 110. Graininess (SN) of an X-ray image depends on the ratio between a signal component and a noise component. The noise component includes an offset error. The signal component varies depending on the conditions of generating X-rays (tube voltage and tube current). When the intensity of the X-rays is high, the signal component is large, and thus, even when the noise component is large, an X-ray image having desired graininess may be acquired. In a case where the amount of the body motion of the patient is large and the coefficient of pressure information fluctuation (coefficient of pressure fluctuation) does not become smaller than the threshold value, when taking an X-ray image is required to be started immediately, by adjusting the conditions of generating X-rays, taking an X-ray image becomes possible.

(Other Embodiments)

Further, the present invention is also implemented by executing the following processing.

Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program. This program and a computer readable recording medium which stores the program are also within the scope of the present invention.

Note that, the above-mentioned embodiments of the present invention are merely specific examples for carrying out the present invention, and should not be construed as limitations on the technical scope of the present invention. Specifically, various variations and modifications are possible without departing from the technical idea or the essential characteristics of the present invention.

The technology according to the present invention may be suitably used in the field of radiographic diagnosis of human beings and animals. Conventionally, pressure applied to a radiation sensor portion itself including a semiconductor is not detected, but pressure applied to a housing of the radiation sensor portion or the like is detected. Conventionally, only whether the body part of the subject is fixed at a predetermined location in the housing of the radiation sensor portion or not is decided. A problem to be solved by the present invention is different from that of the conventional technology. The present invention relates to a technology which determines the timing of photographing at which a stable offset image may be acquired by detecting pressure information fluctuations applied to the radiation sensor portion.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-162430, filed Jul. 25, 2011, which is hereby incorporated by reference herein in its entirety.

What is claimed is:

1. A radiographic apparatus for applying radiation from a radiation source and taking a radiation image, comprising:
    a radiation sensor for acquiring a spatial intensity distribution of radiation as two-dimensional image data;
    a fluctuation detecting unit for detecting fluctuations of the pressure applied to said radiation sensor; and
    an acquisition unit for acquiring, when a coefficient of pressure fluctuation based on fluctuation information which is output from said fluctuation detecting unit, is smaller than a threshold value, at least one of the radiation image and an offset image based on the two-dimensional image data acquired from said radiation sensor.

2. A radiographic apparatus according to claim 1, wherein the pressure fluctuation information is calculated based on the offset image.

3. A radiographic apparatus according to claim 1, further comprising:
    an offset correction unit for making offset correction of the radiation image using the offset image.

4. A radiographic apparatus according to claim 1, wherein the coefficient of pressure fluctuation is calculated based on an acquiring period for the radiation image and the offset image.

5. A radiographic apparatus according to claim 1, wherein the coefficient of pressure fluctuation is calculated with regard to a plurality of sub-regions into which said radiation sensor is divided, and
    the acquisition unit acquires the radiation image and the offset image from the two-dimensional image data when the coefficient of pressure fluctuation is smaller than the threshold value in a central area of the plurality of sub-regions.

6. A radiographic apparatus according to claim 1, wherein the coefficient of pressure fluctuation is calculated based on any one of output of a pressure sensor for measuring the pressure applied to said radiation sensor, the offset image acquired based on the two-dimensional image data, and output of an acceleration sensor placed in said radiation sensor.

7. A radiographic apparatus according to claim 6, wherein the pressure sensor is placed on the back of a surface of said radiation sensor on which the radiation is incident.

8. A radiographic apparatus according to claim 6, wherein, when the pressure sensor is placed between a grid and a surface of said radiation sensor on which the radiation is incident, gain image correction for canceling a transmission image of the radiation of the pressure sensor is made.

9. A radiographic apparatus according to claim 3, wherein the threshold value is determined based on conditions of generating radiation by a radiation source.

10. A control method of controlling a radiographic apparatus for applying radiation from a radiation source and taking a radiation image, comprising:
    detecting fluctuation information on a pressure applied to a radiation sensor;
    acquiring spatial intensity distribution of radiation as two-dimensional image data; and
    acquiring, when a coefficient of pressure fluctuation based on fluctuation information which is output from the fluctuation detecting unit, is smaller than a threshold value, at least one of the radiation image and an offset image based on the two-dimensional image data acquired from the radiation sensor.

11. A control method for a radiographic apparatus, the radiographic apparatus comprising a radiation generating unit for generating radiation and applying the radiation to a subject, and an image detecting unit for detecting as a radiation image radiation which passes through the subject under a state in which radiation is applied to the subject from the radiation generating unit and detecting an offset image under a state in which radiation is not applied to the subject from the radiation generating unit, the method comprising:
    detecting pressure information fluctuations applied to the image detecting unit;
    acquiring the radiation image and the offset image from the image detecting unit when a coefficient of pressure fluctuation based on the pressure information fluctuations detected in the detecting of the pressure information fluctuations is smaller than a threshold value; and
    making offset correction of the radiation image acquired in the acquiring, using the offset image acquired in the acquiring.

12. A non-transitory, computer-readable recording medium having stored therein, in executable form, a program for causing a computer to carry out the control method according to claim 10.

13. A radiographic apparatus according to claim 1, further comprising:
    a control unit for controlling the radiation from the radiation source based on the pressure fluctuation information of the pressure applied to said radiation sensor.

14. A radiographic apparatus according to claim 13, wherein said control unit allows the radiation when an amount of fluctuations acquired from the fluctuation information is equal to or smaller than a predetermined value.

15. A radiographic apparatus according to claim 13, wherein said control unit controls the radiation of the radiation source based on the fluctuation information as output of said fluctuation detecting unit.

* * * * *